US012567498B2

(12) United States Patent
Scholler et al.

(10) Patent No.: US 12,567,498 B2
(45) Date of Patent: Mar. 3, 2026

(54) IMAGE COMPRESSION AND ANALYSIS

(71) Applicant: Wyss Center for Bio and Neuro Engineering, Geneva (CH)

(72) Inventors: Jules René Raymond Scholler, Saint-Cergues (FR); Joel Axel Christopher Jonsson, Dresden (DE); Bevan Leslie Cheeseman, Oxford (GB); Ivo Fabian Sbalzarini, Dresden (DE); Christophe M. Lamy, Renens (CH)

(73) Assignee: Wyss Center for Bio and Neuro Engineering, Geneva (CH)

( * ) Notice: Subject to any disclaimer, the term of this patent is extended or adjusted under 35 U.S.C. 154(b) by 386 days.

(21) Appl. No.: 18/337,883

(22) Filed: Jun. 20, 2023

(65) Prior Publication Data

US 2023/0420114 A1 Dec. 28, 2023

Related U.S. Application Data

(60) Provisional application No. 63/366,818, filed on Jun. 22, 2022, provisional application No. 63/366,825, filed on Jun. 22, 2022.

(51) Int. Cl.
 *G16H 30/40* (2018.01)
 *G06T 5/20* (2006.01)
 (Continued)

(52) U.S. Cl.
 CPC .............. *G16H 30/40* (2018.01); *G06T 5/20* (2013.01); *G06T 7/11* (2017.01); *G06T 7/70* (2017.01);
 (Continued)

(58) Field of Classification Search
 CPC .......... G16H 30/40; G16H 30/20; G06T 5/20; G06T 7/11; G06T 7/70; G06T 9/00;
 (Continued)

(56) References Cited

U.S. PATENT DOCUMENTS

2009/0208098 A1 8/2009 Yang
2019/0130570 A1* 5/2019 Jackson ................ G06T 7/0014
(Continued)

FOREIGN PATENT DOCUMENTS

WO 2023/248141 A1 12/2023

OTHER PUBLICATIONS

Baum et al., "High-Throughput Segmentation of Tiled Biological Structures using Random-Walk Distance Transforms", Integrative and Comparative Biology, vol. 59, No. 6, Jul. 8, 2019, pp. 1700-1712. (Year: 2019).*

(Continued)

*Primary Examiner* — Jennifer Mehmood
*Assistant Examiner* — Jose M Torres
(74) *Attorney, Agent, or Firm* — Hamilton, Brook, Smith & Reynolds, P.C.

(57) ABSTRACT

An efficient image analysis, processing, and handling based on adaptive particle representation (APR) for processing large scale color image datasets is disclosed. Analyzing large biological mass or tissue samples is achieved at 100+ times faster computation and at improved memory and storage compression ratios. Embodiments are well suited for large 3D cleared tissue samples, large-scale imaging projects such as whole-brain mapping initiatives and human neurohistopathology. A datastore holds adaptive sampling representations of tiles, individual tile positions, and corresponding other image data of a biological mass of interest. An image output using single loading of tiles from the datastore supports a complete image at full resolution of the biological mass.

39 Claims, 8 Drawing Sheets
(3 of 8 Drawing Sheet(s) Filed in Color)

(51) Int. Cl.

| | |
|---|---|
| *G06T 7/11* | (2017.01) |
| *G06T 7/70* | (2017.01) |
| *G06T 9/00* | (2006.01) |
| *G06V 10/10* | (2022.01) |
| *G06V 10/44* | (2022.01) |
| *G16H 30/20* | (2018.01) |
| *H04N 19/132* | (2014.01) |
| *H04N 19/14* | (2014.01) |
| *H04N 19/154* | (2014.01) |
| *H04N 19/167* | (2014.01) |
| *H04N 19/17* | (2014.01) |

(52) U.S. Cl.
CPC ............... *G06T 9/00* (2013.01); *G06V 10/16* (2022.01); *G06V 10/44* (2022.01); *G16H 30/20* (2018.01); *H04N 19/132* (2014.11); *H04N 19/14* (2014.11); *H04N 19/154* (2014.11); *H04N 19/167* (2014.11); *H04N 19/17* (2014.11)

(58) Field of Classification Search
CPC ........ G06V 10/16; G06V 10/44; H04N 19/14; H04N 19/154; H04N 19/167; H04N 19/17; H04N 19/132
See application file for complete search history.

(56) References Cited

U.S. PATENT DOCUMENTS

2020/0043134 A1    2/2020  Martin et al.
2023/0401720 A1*  12/2023  Cobanoglu ............ G06V 10/46

OTHER PUBLICATIONS

Berg, S., et al., "ilastik: interactive machine learning for (bio)image analysis", Nature Methods, vol. 6, Dec. 2019, pp. 1226-1232.
Bria, A., et al., "TeraStitcher—A tool for fast automatic 3D-stitching of teravoxel-sized microscopy images", BMC Bioinformatics, vol. 13, No. 316, 2012, 15 pages.
Cheeseman, B. L., et al., "Adaptive particle representation of fluorescence microscopy images", Nature Communications, vol. 9, Article No. 5160, 2018, 101 pages.
Fernandez-Delgado, M., et al., "Do we Need Hundreds of Classiers to Solve Real World Classifcation Problems?", Journal of Machine Learning Research, vol. 15, 2014, pp. 3133-3181.
Guizar-Sicairos, M., et al., "Efficient subpixel image registration algorithms", Optics Letters, vol. 33, Issue 2, 2008, pp. 156-158.
International Search Report and Written Opinion received for PCT Patent Application No. PCT/IB2023/056392, mailed on Nov. 6, 2023, 15 pages.
Jonsson, J., et al., "Parallel Discrete Convolutions on Adaptive Particle Representations of Images", arxiv.org, Dec. 7, 2021, pp. 5-6.
Lein, Ed. S., et al., "Genome-wide atlas of gene expression in the adult mouse brain", nature, vol. 445, Jan. 11, 2007, pp. 168-176.
Li, C. H., et al., "An iterative algorithm for minimum cross entropy thresholding", Pattern Recognition Letters, vol. 19, No. 8, Jun. 1998, pp. 771-776.
Lowe, D. G., et al., "Distinctive Image Features from Scale-Invariant Keypoints", International Journal of Computer Vision , vol. 60, Nov. 2004, pp. 91-110.
Niedworok, C. J., et al., "aMAP is a validated pipeline for registration and segmentation of high-resolution mouse brain data", Nature Communications, vol. 7, 2016, 9 pages.
Padfield, D., "Masked Object Registration in the Fourier Domain", IEEE Transactions on Image Processing, vol. 21, No. 5, May 2012, pp. 2706-2718.
Scholler, J., et al., "Efficient image analysis for large-scale next generation histopathology using Paprica", BioRxiv, Jan. 28, 2023, XP093094554.
Scholler, J., et al., "Leveraging the Adaptive Particle Representation for Efficient Large-Scale Neurohistology", Poster Presentation at the European Light Microscopy Initiative 2021, Jun. 24, 2021.
Scholler, J., et al., Leveraging the Adaptive Particle Representation for Efficient Large-Scale Neurohistology, Jan. 28, 2023, (15 pages).
Sofroniew, N., et al., "napari/napari: 0.4.15", available online <https://zenodo.org/records/6344271>, Mar. 10, 2023, 4 pages.
Tyson, A. L., et al., "Tools for accurate post hoc determination of marker location within whole-brain microscopy images", bioRxiv, May 23, 2021, 25 pages.

* cited by examiner

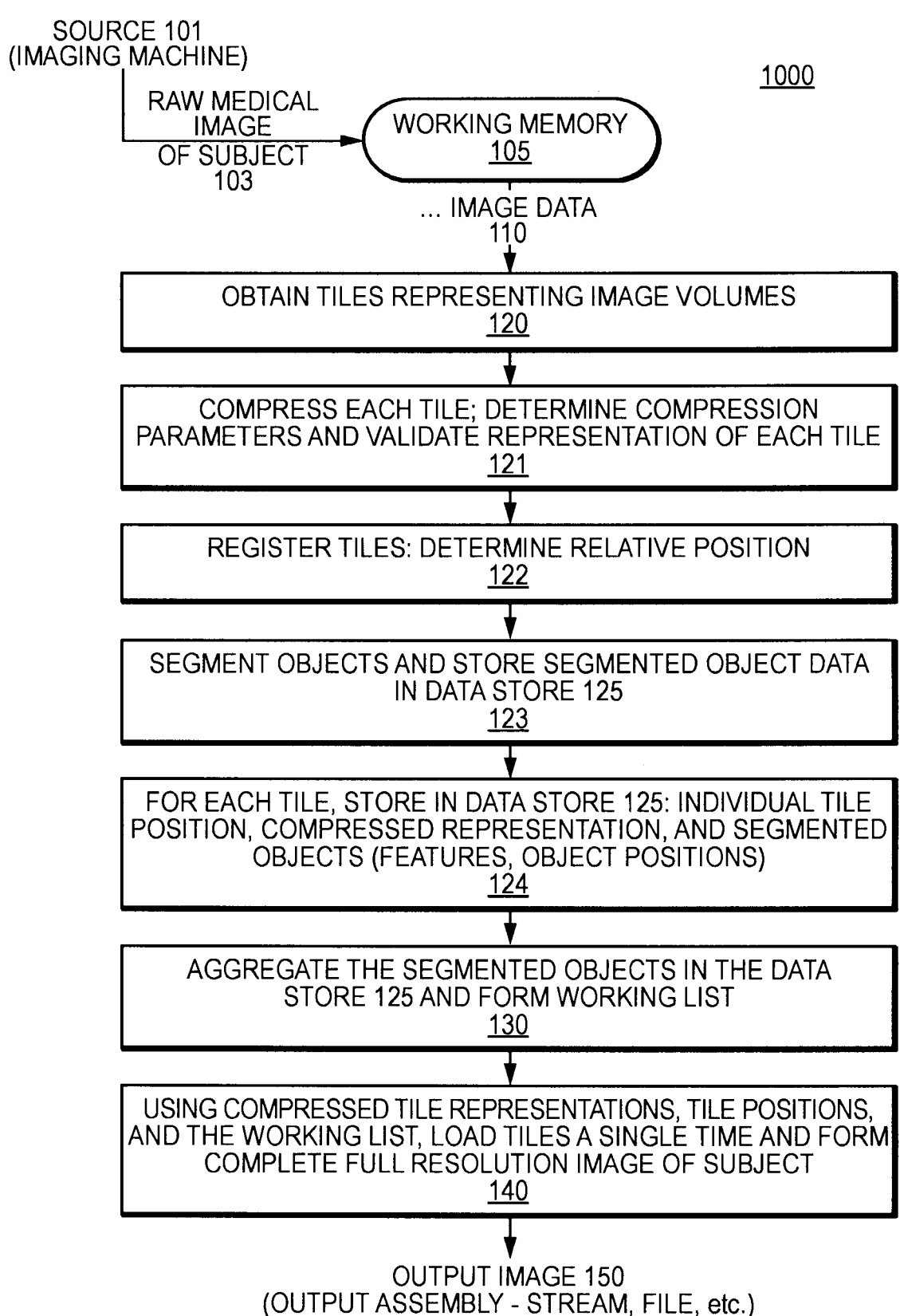

SOURCE 101
(IMAGING MACHINE)

1000

RAW MEDICAL
IMAGE
OF SUBJECT
103

WORKING MEMORY
105

... IMAGE DATA
110

OBTAIN TILES REPRESENTING IMAGE VOLUMES
120

COMPRESS EACH TILE; DETERMINE COMPRESSION
PARAMETERS AND VALIDATE REPRESENTATION OF EACH TILE
121

REGISTER TILES: DETERMINE RELATIVE POSITION
122

SEGMENT OBJECTS AND STORE SEGMENTED OBJECT DATA
IN DATA STORE 125
123

FOR EACH TILE, STORE IN DATA STORE 125: INDIVIDUAL TILE
POSITION, COMPRESSED REPRESENTATION, AND SEGMENTED
OBJECTS (FEATURES, OBJECT POSITIONS)
124

AGGREGATE THE SEGMENTED OBJECTS IN THE DATA
STORE 125 AND FORM WORKING LIST
130

USING COMPRESSED TILE REPRESENTATIONS, TILE POSITIONS,
AND THE WORKING LIST, LOAD TILES A SINGLE TIME AND FORM
COMPLETE FULL RESOLUTION IMAGE OF SUBJECT
140

OUTPUT IMAGE 150
(OUTPUT ASSEMBLY - STREAM, FILE, etc.)

FIG. 3B 50, 60

| | | |
|---|---|---|
| I/O DEVICES INTERFACE 82 | CENTRAL PROCESSOR UNIT 84 | NETWORK INTERFACE 86 |

SYSTEM BUS 79

MEMORY
90

ROUTINE
92

DATA
94

DISK STORAGE
95

OS PROGRAM
92

DATA
94

IMAGE COMPRESSION AND ANALYSIS

RELATED APPLICATIONS

This application claims the benefit of U.S. Provisional Application No. 63/366,818, filed on Jun. 22, 2022, and U.S. Provisional Application No. 63/366,825, filed on Jun. 22, 2022. The entire teachings of the above applications are incorporated herein by reference.

BACKGROUND

Biological and medical imaging are a subset of digital imagery and refer to the technology area that generates and renders images of internal body parts and growths including tissues, organs, skeletal structures, tendons, ligaments, and some blood vessels. There are a variety of medical image producing techniques and machines such as confocal and light-sheet microscopy, x-ray systems, CT (computed tomography) scanners, MRI (magnetic resonance imaging) machines, ultrasound systems, and PET (positron emission tomography) scanners, to name a few. The rendered images are digital visualizations that enable physicians to diagnose and treat patients, and more particularly allow physicians to find diseases, abnormalities, and injuries. For instance, CT scans provide a series of images of 2D slices or cross-sections of the body that enable a physician to view digitized on a computer display screen a tumor, its shape, size, and location, and blood vessels that feed the tumor.

Researchers and attending physicians alike rely on biological and medical images. Typical modalities of these imaging processes, and generally speaking digital imaging systems, include image acquisition (such as by one of the above-mentioned machines or technologies), archiving the acquired raw digital images, retrieval, processing (analyses), communication/distribution, and display. Image data and their corresponding digital files for certain biological or medical research can be relatively voluminous posing problems with computer memory storage (archiving) and speed with which computer retrieval, processing (analyses), and display occurs. For example, color images of tissue samples of whole mouse brains or large human brain sections, and other annotated medical images are relatively large digital files. Various image compression algorithms exist but are mostly used for storing files because reading and understanding the content of a file would require uncompressing it, reverting the benefit of the compression.

SUMMARY

Embodiments of the present invention address the shortcomings in the art for handling (processing for analytics, communicating/distributing, displaying, etc.) and managing (storing in computer memory, archiving, retrieving, communicating, etc.) certain medical image data, in particular, large volume, multi-dimensional image data. Embodiments advantageously provide faster processing and improved ability to store image files in computer memory without requiring upscaling of processor resources or memory.

Embodiments provide computer-based systems and computer-implemented methods of improved multi-dimensional image/medical image/biomedical image handling (e.g., processing analysis, distribution, display) and management (e.g., storage, retrieval, communication, etc.). In particular, embodiments achieve relatively large image data storage (archiving), retrieval, analysis, processing, and display at acceptable speeds without requiring (in a manner free of)

additional memory or processor resources. The relatively large image data includes, for non-limiting example, biological and medical images generated by any of: confocal and light-sheet microscopes (other optical microscopes including but not limited to widefield, super resolution, and electron microscopes), x-ray, computed tomography (CT), positron emission tomography (PET), optical coherence tomography (OCT), MRI, ultrasound, and other digital imaging technology.

The image data may be multidimensional and include in addition to the digitized subject image: color, annotations (e.g., researcher or physician text, notes, and/or markings), graphics, a temporal or time dimension, and the like.

Subjects of the relatively large image data are, for non-limiting example, tissue samples, whole mouse brains, human brain sections, other mammalian brains or parts thereof, or other biological mass or biological material of interest.

In one embodiment, for given image data of a biological mass, a computer-implemented image handling method obtains, accesses, or otherwise receives a sequence of cross-sectional images (two-dimensional image units, generally) at increasing depth along an axis in a third spatial dimension. Each two-dimensional image unit or cross section is an $n \times m$ pixels frame in a respective parallel plane orthogonal to the axis. The method obtains different sequences of two-dimensional image units at increasing depth along respective orthogonal axes. Each two-dimensional unit of a sequence is an $n \times m$ pixels frame in a respective parallel plane orthogonal to the respective axis of the sequence. The respective orthogonal axes of different sequences are at different frame positions across the respective planes. As a result, the method obtains a plurality of sequences (so called tiles) representative of image volumes capturing in three spatial dimensions different portions of the biological mass. Different sequences or tiles of the resulting plurality represent different image volumes obtained from the given image data.

Accordingly, as used herein, a 'frame' is a two-dimensional (2D) $n \times m$ pixel array of data. Multiple such 2D arrays (frames) taken successively along the same orthogonal axis constitute a 3D data array referred to as a 'tile' herein. Different tiles (successions of frames) have different orthogonal axes along which the respective succession of frames have been taken. Restated, one tile is formed of a respective succession of frames taken along one orthogonal axis. A second tile is formed of a respective succession of frames taken along another orthogonal axis. A third tile has its succession of frames taken along that tile's orthogonal axis, and so forth.

Next, during image acquisition, the method automatically, independently, digitally processes each tile (sequence) by:
  i. Compressing image data of tile areas of low information content and maintaining full or high resolution of high information content areas resulting in an adaptive sampling representation of the tile;
  ii. Automatically determining conversion parameters for the tile;
  iii. Automatically comparing the compressed data and the raw data to validate that the converted data captures the required information;
  iv. Computing a maximum intensity projection of the tile in multiple spatial directions and for each edge where there is a neighboring tile;
  v. Registering the tile with other neighboring tiles by: computing pair-wise registration in 3 spatial dimensions between each neighboring tile using the computed maximum intensity projections. Subsequently to image acquisition, embodiments globally optimize tile position for a reliability measure. The resulting relative tile positions enable stitching to be performed with a single loading of each tile, and enable the stitching to reconstruct the image volumes; and vi. Storing in a datastore in computer memory the adaptive sampling representation of the tile, the determined conversion parameters for the tile, and an indication of spatial position of the tile. The step of storing is in a manner that the datastore stores individual tile positions and reduced amounts of the given image data instead of storing raw data of source images of the biological mass.

As heretofore unachieved in the prior art, embodiments provide efficient image processing (using a compressed form of the image data for the analysis) and scalability (analyzing tiles independently) as follows. During image acquisition, for a given tile, the method: (i) applies a classifier in a manner segmenting objects from the given tile including extracting object features and object positions, and (ii) aggregates and stores the segmented objects in the datastore. Objects that appear twice or more on neighboring tile areas are automatically merged by means of a matching algorithm, for non-limiting example by: (a) finding the nearest neighbors in the feature space where one considers each object position (in the final sample space, after registration), size, and shape; and (b) checking that the match is reliable using Lowe criteria (the second nearest neighbor has to be farther by a predefined margin). Other matching algorithms are suitable. Next, embodiments can subsequently (post-acquisition of the source image) stitch together and reconstruct the subject image with a single loading of each tile as represented in the datastore or from corresponding data in the datastore (i.e., the stored compressed image data, stored relative tile position, compression parameters, stored segmented objects, and stored object positions). As such, embodiments avoid the problems of prior art where object segmentation and other analyses are applied to the whole image file which may become too large to handle or to be saved.

Lastly, the method forms an image output using single loading of tiles (instead of loading a tile multiple times or at different times) from the datastore (that is, the compressed image data and corresponding data) that supports a complete image at full resolution of the biological mass. Using the stored compressed image data, stored relative tile position, compression parameters, stored segmented objects, and stored object positions from the datastore relieves necessity of additional computer memory and/or processor resources for any of: storing, retrieving, communicating, distributing, processing, analyzing, displaying, and combinations thereof of the complete image.

In embodiments, the compressing of tile areas of low information content includes employing the Adaptive Particle Representation techniques.

A computer-implemented image handling method, comprises: (A) for given image data of a biological mass, obtaining a sequence of two-dimensional image units at increasing depth along an axis in a third spatial dimension, each two-dimensional image unit being an n×m pixels frame in a respective parallel plane orthogonal to the axis, obtaining different sequences of two-dimensional image units at increasing depth along respective orthogonal axes, each two-dimensional image unit of a sequence being an n×m pixels frame in a respective parallel plane orthogonal to the respective axis of the sequence, different sequences having different orthogonal axes at different tile positions across the respective planes, the obtaining resulting in a plurality of sequences serving as tiles and representative of image volumes capturing in three spatial dimensions different portions of the biological mass, different sequences of the plurality being different tiles representing different image volumes.

In some embodiments during source image acquisition (and in other embodiments at another time), the method (B) automatically processes tile by tile, that is processes each tile independently by: (i) compressing image data of tile areas of low information content and maintaining high (full) resolution of high information content areas resulting in an adaptive sampling representation of the tile, (ii) determining relative tile position with respect to other tiles, (iii) segmenting the adaptive sampling representation of the tile for objects of interest, the segmenting including extracting object features and respective object positions, and (iv) storing in a datastore in computer memory, the adaptive sampling representation of the tile, an indication of the determined tile position, the segmented objects, the extracted respective object features, and object positions. The storing is performed in a manner such that the datastore stores individual tile positions and reduced amounts of the given image data instead of storing source images of the biological mass.

As next steps, the method: (C) aggregates the segmented objects stored in the datastore, wherein aggregating includes automatically merging segmented objects that appear twice or more on neighboring tiles resulting in a working list of segmented objects stored in the datastore. And (D) based on the adaptive sampling representations of tiles, tile positions, and the working list of segmented objects as stored in the datastore, the method loads tiles a single time and forms a complete image at full resolution of the biological mass, in part or in whole. Restated, the method does not require loading of tiles multiple times or at different times in order to achieve ease of storage and to perform image analytics (e.g., object segmentation). As configured, the single loading of tiles relieves necessity of additional computer memory and/or processor resources for any of: storing, retrieving, communicating, distributing, processing, analyzing, displaying, and combinations thereof of the complete image.

The working list may include indications of the segmented objects, object positions, and respective features.

In embodiments, processing each tile independently further includes: (i) automatically determining compression parameters used to compress image data of the tile; (ii) storing the determined compression parameters in the datastore; and (iii) automatically comparing the resulting adaptive sampling representation and source image data in a manner validating that the adaptive sampling representation captures required information of the given image data.

In embodiments, determining relative tile position of a tile includes: (i) computing a maximum intensity projection of the tile in multiple spatial directions and for each edge of the tile where there is a neighboring tile; (ii) computing tile pair-wise registration parameters with already acquired neighboring tiles; and (iii) storing the computed tile pair-wise registration parameters in the datastore. The computing of tile pair-wise registration parameters is accomplished by: for each edge of the tile where there is a respective acquired neighboring tile, correlating the computed maximum intensity projection of the edge of the tile to a computed maximum intensity projection of a corresponding edge of the respective acquired neighboring tile. As a result, the method achieves increased precision of the relative tile position of the tile with respect to neighboring tiles.

In embodiments, tile registration further includes global optimization. Specifically, subsequent to image acquisition, the method globally optimizes all the stored pair-wise registration results for a reliability measure, such that all tile positions are precisely corrected. The added precision and correction of relative tile position further enables: (a) stitching of image data corresponding to tiles, (b) proper reconstruction of the whole biological mass; and (c) reliable extraction of high-level information on the imaged biological mass, such as, but not limited to, volume of the biological mass, and number of segmented objects inside. In embodiments, step C (aggregation of segmented objects) is performed after global optimization.

In embodiments, the given image data comprises biological or medical images acquired and generated by any of: optical microscopy or optical microscopes (including but not limited to widefield, confocal, super resolution, electron, and light-sheet microscopes), x-ray, computed tomography, positron emission tomography, optical coherence tomography, magnetic resonance imaging, ultrasound, and other digital imaging techniques. For a subject tile, step A and step B are accomplished during acquisition of the biological or medical images, and step C is performed subsequent to acquisition of images corresponding to the subject tile.

In embodiments, the biological mass is any of: a tissue sample, whole mouse brain, human brain section, other mammalian brain portion, and other biological material of interest.

In embodiments, one or more digital processors perform in automated fashion the steps of the method described herein. Other embodiments provide computer-based systems, computer program products, and software as a service (SaaS). A computer-based system embodying the present invention may be formed of an interface, a datastore in computer memory, and processor executable working modules operatively coupled between the interface and datastore. The interface receives or accesses subject image data of a biological mass of interest. The working modules are responsive to the interface and configured (programmed) to automatically perform on the image data the image compression by adaptive sampling representation (e.g., APR), tile registration, and object segmentation and aggregation. For each tile, the datastore holds the adaptive sampling representation, determined relative tile position, segmented objects, and respective object position, and extracted features. From contents of the datastore, the system produces, with a single loading of tiles, a complete image at full resolution of the biological mass in part or whole. The single loading of tiles relieves necessity of additional computer memory and/or processor resources for any of: storing, retrieving, communicating, distributing, processing, analyzing, displaying, or any combination of handling and managing the complete image.

In embodiments, the stored adaptive sampling representation of each tile is merged and cropped on overlapping areas so that a physical position in the biological mass is uniquely described by a single particle in the adaptive sampling representations of tiles stored in the datastore. For a given overlap area, where two or more tiles form the overlap, the adaptive sampling representations of the overlap area are merged into one of the tiles and cropped from the remaining of the two or more tiles. The merged and cropped versions of the adaptive sampling representations of the tiles are stored in the datastore. In this way, the adaptive sampling representations (merged and cropped on overlapping areas) of tiles provide efficiencies in image data storage and handling as heretofore unachieved.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 3B is a flow diagram of an embodiment of the present invention.

FIG. 6A illustrates four overlapping tiles with overlap to neighboring tiles on the left and right, above and below. FIG. 6B illustrates the tiles in FIG. 6A with the adaptive sampling representations of the tiles modified by merging and cropping of overlap areas.

DETAILED DESCRIPTION

A description of example embodiments follows.

Adaptive Particle Representation (APR) is an efficient, content-adaptive, image representation technique that also provides data compression. The APR adaptively represents the content of an image while maintaining image quality. By providing data compression, APR reduces image storage costs but also advantageously overcomes memory and processing bottlenecks by directly being used in image processing tasks without a translation back to pixel data. See B. L. Cheeseman, et al, "Adaptive particle representation of fluorescence microscopy images," Nature Communications 9, no. 5160, 4 Dec. 2018.

For a subject image or image volume, the APR replaces pixels or voxels with particles (points in space that carry intensity) positioned according to image content. Particles can be placed wherever image contents require, and particles may have different sizes in different parts of the image. The different sizes define respective resolution with which the image is locally represented. The required resolution is represented by an Implied Resolution Function, which attributes high resolution to image areas where the intensity rapidly changes in space (e.g., edges), and low resolution to image areas with low variation in intensity (e.g., background, or uniform foreground). The Implied Resolution Function defines the radius of a neighborhood around each pixel. At any pixel location, the image intensity value can be reconstructed within a user-set error threshold by taking any non-negative weighted average of the particle intensities contained in this neighborhood. Since illumination conditions, and therefore intensity ranges, can vary greatly between different regions within a sample, the errors considered are normalized with respect to a local intensity scale.

Restated, APR uses spatially adaptive sampling to resample an image guided by local information content while using local gain control. The resulting output, from applying APR to an image, is a representation of the image formed of a set of particles with associated intensity values.

Principles of the present invention leverage techniques of the Adaptive Particle Representation for efficient image analysis and processing of relatively large-scale image datasets. Embodiments achieve analysis of large biological mass or tissue samples at 100+ times faster computation rates and at improved memory and storage compression ratios. Embodiments are well suited for large-scale medical or biomedical imaging projects such as whole-brain mapping initiatives and human neurohistopathology, for non-limiting example. Embodiments are also well suited for sequential analysis of the same sample type, e.g., a mouse brain, when experiments have to be repeated for statistical purposes.

Figure 3A:
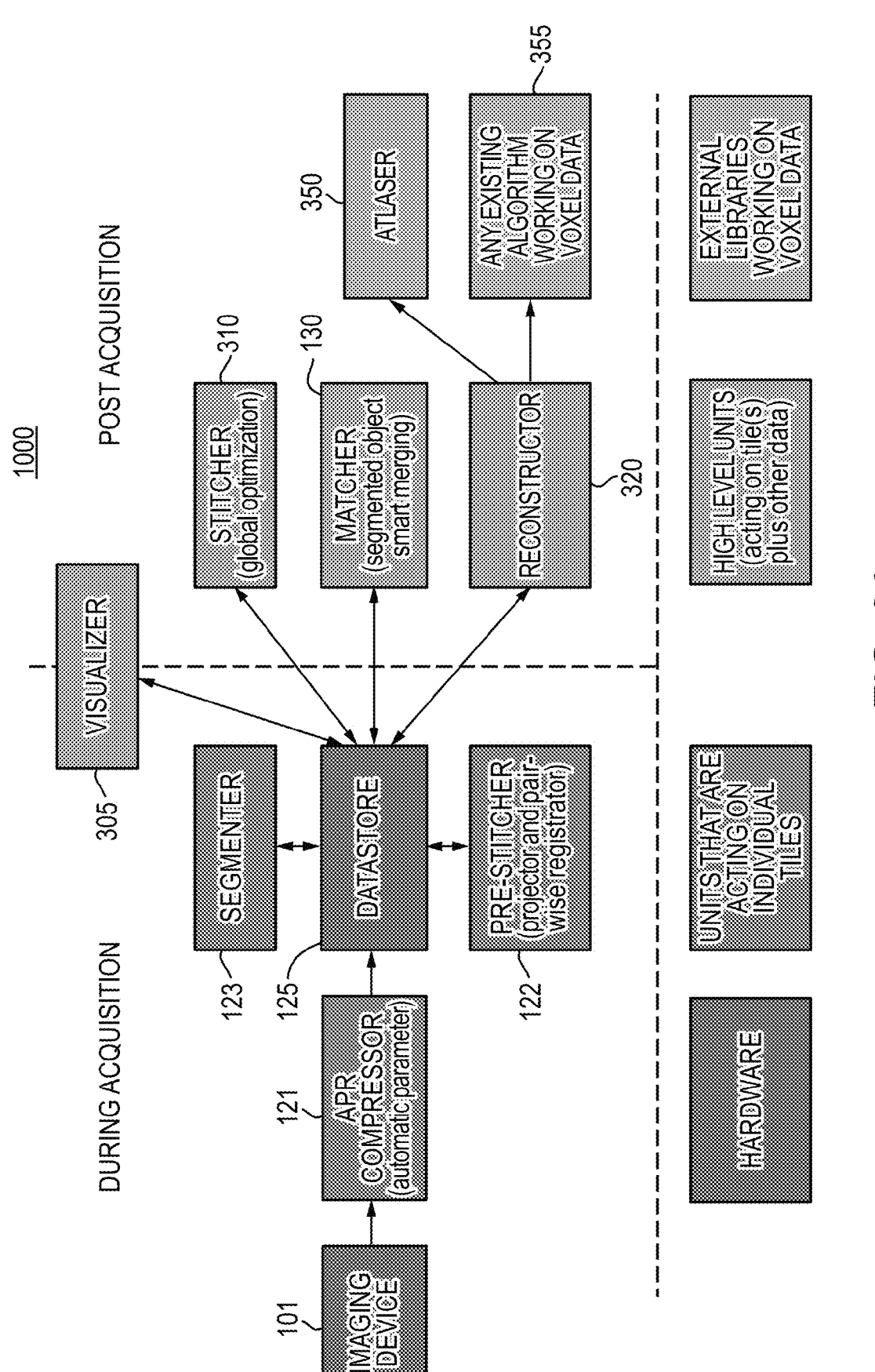
FIG. 3A is a block diagram of an embodiment with a key at the bottom row.

FIGS. 3A and 3B illustrate the flow of data and control in methods and systems 1000 embodying principles of the present invention. Although illustrated and described in an end-to-end pipeline from source imaging machine to an end utility image for distribution, storage, and communication, embodiments are not so limited. Different embodiments or parts thereof can serve as an image compression tool or apparatus, an image storage and retrieval method and system, an image analysis and post processing method and system, and the like. For purposes of illustration and not limitation, in such context FIGS. 3A and 3B are discussed next and followed by further description of implementation details.

The key at the bottom row in FIG. 3A includes hardware indicated in blue (darkest gray or standard diagonal hatch pattern); units acting on individual tiles indicated in orange (medium gray or conventional cross hatching); high level units (acting on tiles plus other data) indicated in green (medium dark gray or dotted pattern); and external libraries working on voxel data indicated in light grey (or solid white background). By this key, the hardware elements of embodiments include imaging device 101 and datastore 125. Units that act on individual tiles include: APR compressor (with automatic conversion parameters) 121, segmenter 123, and pre-stitcher (with projector and pair-wise registration) 122. High level units include: visualizer 305, stitcher (with global optimizer) 310; matcher (segmented object smart merging) 130; and reconstructor 320. Examples of external libraries include Atlaser 350 and other algorithms 355 working on voxel data.

In an embodiment system 1000, a source imaging machine 101, such as a microscope, acquires and generates biological or medical images 103 of a subject biological mass, e.g., an organ, body part, tissue, or biological material of interest. It is understood by those skilled in the art that various source imaging machines (confocal and light-sheet microscopes, OCT scanners, CAT scanners, PET scanners, ultrasound systems, MRI systems, x-ray systems, etc.) 101 can be utilized. Other optical microscopy techniques or electron microscopy techniques may serve as the source imaging machines 101 (optical type microscopes) including, but not limited to, widefield microscopes, super resolution microscopes, and electron microscopes. Other digital imaging techniques are suitable. The raw biological or medical images 103 (FIG. 3B) can be of large scale (or relatively large volume as compared to general common place digital images). In some embodiments, the medical or biomedical images 103 are of large human brain sections, whole mouse brains, or other mammalian brains in part or whole, for non-limiting example.

The source 101 acquires and provides the raw biomedical images 103 to local memory, computer storage, sharable memory, archives, and the like at 105 (generally referred to as working memory, FIG. 3B). In working memory 105, researchers, physicians and other users may add annotations (text notes, markings, etc.), graphics, and/or color to the raw biological or medical images 103. The resulting image data 110 is thus formed of multiple dimensions of information, i.e., the raw biomedical image 103 plus annotations, graphics, and color. Each pixel of the image data 110 is represented by an n-tuple. N-tuple data representations are implemented by linked lists, arrays, or other data structures storing the multiple dimensions of information per pixel. The different dimensions (or tuples) of information per pixel may include: raw source image (digital image pixel value), annotation or graphics (overlay value), color (red, green, blue factor values), and other layers or types of information such as for non-limiting example, a second or more layers of text or graphics, fluorescent channel indicia, time dimension, indications of blood pressure or flow, other physical conditions, etc. In one embodiment, one channel or tuple is of concern and thus there is one value instead of the multiple per pixel.

System and method 1000 of the present invention obtain, access, or otherwise receive the image data 110 (n-tuples of data per pixel) of the subject biological mass, either in near real time during source 101 acquisition or post-acquisition, from working memory 105. In particular, an interface 120 (FIG. 3B) receives the image data 110 and accesses or otherwise obtains therefrom a sequence of cross-sectional images (2-dimensional image units, generally) at increasing depth along an axis in a third spatial dimension. Each 2-dimensional image unit is an n×m pixels frame in a respective parallel plane orthogonal to the axis in the third dimension. The sequence of frames along the subject axis is called a tile. The interface 120 obtains different tiles, that is, sequences of cross-sectional images (2-dimensional image units or frames) along respective axes. Each 2-dimensional image unit of a sequence (tile) is an n×m pixels frame in a respective parallel plane orthogonal to the respective axis of the sequence. Different sequences or tiles are at different tile positions across the respective planes.

As a result, interface 120 obtains a plurality of such sequences or tiles. Each sequence/tile in the plurality represents an image volume capturing in three spatial dimensions (3D space) a respective portion of the subject biological mass in the image data 110. Different sequences/tiles represent different image volumes, and the different image volumes capture different portions of the subject biological mass.

A tile processing module 121, 122, 123, 124 is coupled to communicate with the interface 120. During source image acquisition, for each sequence/tile obtained at interface 120, the tile processing module 121, 122, 123, 124 processes each tile as follows. First the tile processing module at step 121 compresses tile areas of low information content and maintains full resolution of high information content areas. This results in an adaptive sampling representation of the tile. In embodiments, APR is utilized to accomplish such image compression and adaptive sampling of the tile. Other adaptive sampling techniques are suitable.

Next, the tile processing module 121 automatically determines conversion parameters used to compress image data of the tile. In embodiments, the conversion parameters (or compression parameters herein) are automatically determined by algorithms and techniques detailed below. In some embodiments, tile processing module 121 may use APR independently on different channels or dimensions (tuples) of image data 110 of a tile. For non-limiting example, tile processing module 121 may apply APR independently to the fluorescent channel and automatically determine corresponding compression parameters for the same tile. Module steps 121, 124 store the compressed tile (i.e., the adaptive sampling representation of the tile), and the corresponding determined compression parameters in a datastore 125.

Module 121 also validates the compressed representation of the tile by automatically comparing the resulting adaptive sampling representation and source image data. The comparison determines whether the adaptive sampling representation captures required information of the source image data. Known or common techniques such as peak signal to noise ratio, structural similarity index, or the like are used in the validating comparison at module step 121.

Figure 6A:
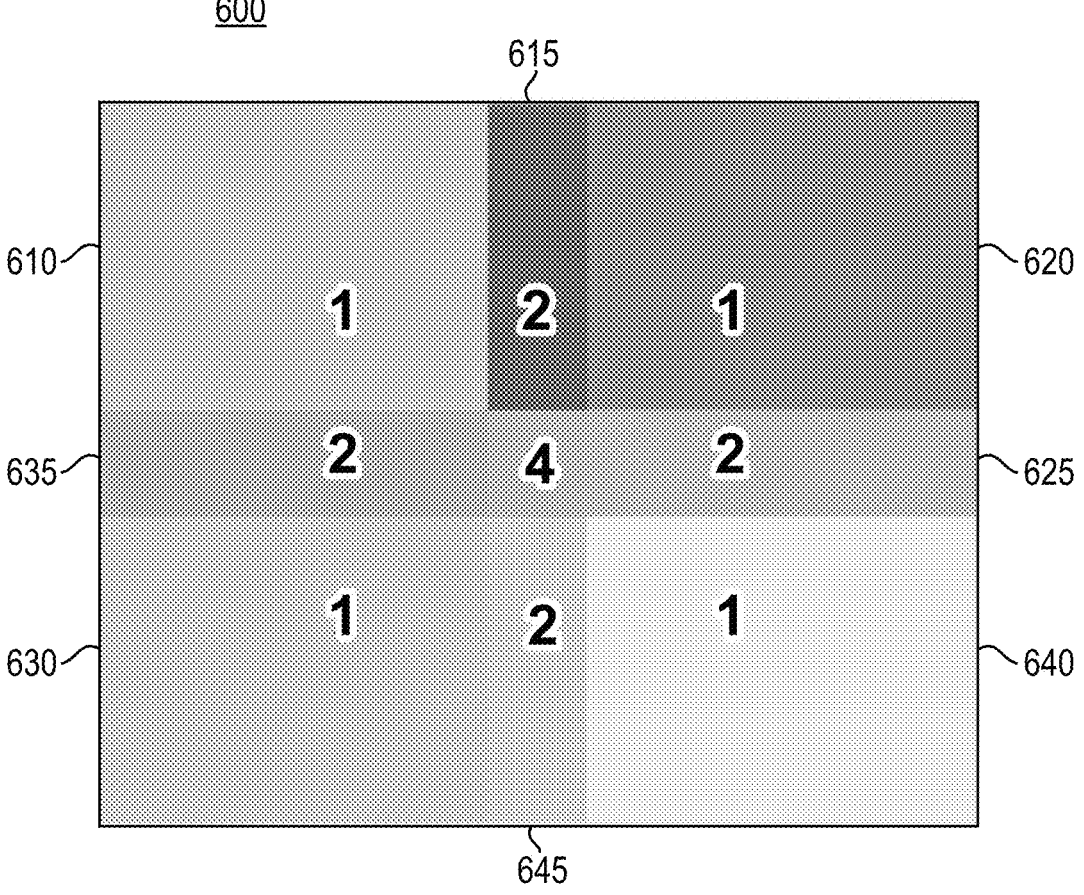
FIGS. 6A and 6B are schematic illustrations of merging and cropping image data of overlapping tiles in embodiments of the present invention.

Embodiments may provide improvements in compressed image data representation of overlapping areas of neighboring tiles stored in datastore 125. In embodiments, module 121 stores each tile separately in datastore 125, and the datastore 125 contains the original compressed data (adaptive sampling representation) where each neighboring tile has an overlapping area with its neighbors. In such a configuration, a physical position in the biological mass (physical sample that is being imaged) is not always uniquely defined by a single particle (of the adaptive sampling representations) in the datastore 125, but can be defined by 2 particles (adjacent neighboring areas) or 4 particles (corner overlapping areas). FIG. 6A illustrates this phenomenon where 4 different tiles (represented with different colors) are overlapping.

The schematic drawing of FIG. 6A is illustrative where the numerals 1, 2, and 4 indicate the number of compressed image particles (adaptive sampling representation particles) that define a spatial position in the biological mass. Specifically, a block or quadrant 600 of four tiles is shown. In practice one has many more tiles, but the principle remains the same. The top left tile 610 overlaps along the length of its right-hand side edge the neighboring tile 620 to the right, i.e., the top right tile of the block 600. The top left tile 610 overlaps along its bottom edge the neighboring tile 630 below, i.e., the lower left tile of the block 600. In a like fashion, the top right tile 620 overlaps along the left-hand side edge the top left tile 610. The top right tile 620 overlaps along its bottom edge the neighboring tile 640 below it, i.e., the lower right tile of the block 600. The lower left tile 630 of the quadrant (block 600) overlaps along its upper edge the top left tile 610. The lower left tile 630 overlaps along its right-hand side edge the lower right tile 640. The lower right tile 640 overlaps along its left-hand side edge the lower left tile 630. The lower right tile 640 overlaps along its upper edge the top right tile 620.

Each non-overlapping tile area is marked with a numeral 1 to indicate that a single particle (of the adaptive sampling representation of the respective tile) in the datastore 125 uniquely defines the represented spatial location in the subject biological mass (physical sample being imaged).

Each area that is an overlap of 2 tiles is marked with a numeral 2 to indicate that two particles (one from each compressed image/adaptive sampling representation of the adjacent neighboring tiles) in the datastore 125 define the corresponding spatial location in the subject biological mass. For non-limiting example, the area of overlap 615 between top left tile 610 (along its right side edge) and top right tile 620 (along its left side edge), not including or minus their overlapping interior corner area toward the center of block 600, is marked with a numeral 2 indicating that two particles (one from each of the two sets of particles of the respective adaptive sampling representations of tiles 610 and 620) in the datastore 125 define the corresponding position or spatial location in the biological mass of interest. Likewise, the overlap area 625 (between top right tile 620 and lower right tile 640), overlap area 635 (between top left tile 610 and lower left tile 630), and overlap area 645 (between lower left tile 630 and lower right tile 640), minus respective overlapping interior corner areas, are each marked with a numeral 2 to indicate that two particles (from respective sets of particles of the adaptive sampling representations of the two adjacent neighboring tiles) in the datastore 125 define the corresponding position (spatial location) in the biological mass.

The area of overlap of all four tiles 610, 620, 630, 640 (their interior corners, i.e., the lower right corner of top left tile 610, the lower left corner of top right tile 620, the upper right corner of lower left tile 630, and the upper left corner of lower right tile 640) is marked with the numeral 4 to indicate that four particles from respective sets of particles corresponding to the adaptive sampling representations of the four adjacent neighboring tiles 610, 620, 630, 640 in the data store 125 define the corresponding spatial location or position in the biological mass.

An interesting improvement in other embodiments: a) merges the particle information of overlapping tile areas toward storing the merged result in datastore 125, and b) crops the tiles (representations thereof) so a spatial location or point position in the sample of interest (biological mass) is uniquely defined by a particle in one stored tile, that is, uniquely by a single particle in datastore 125. Continuing with the FIG. 6A example, the improved embodiment shown in FIG. 6B merges 690 particle information (from adaptive sampling or otherwise compressed image data representations) on overlapping tile areas by (i) retaining the smallest particles (representing the highest resolution) in the union of the sets of particles corresponding to the subject overlapping tile area. Next the merging method 690: (ii) for each set of particles involved in the overlap, averages the intensity values of the particles in the set (average per tile area), (iii) across the subject overlapping tile areas, selects the maximum of the calculated average intensity values, and (iv) assigns the outcome of (iii) as the intensity value to the retained smallest particles of step (i). Lastly, the method 690 crops the affected tiles (representations thereof) so that any position in the subject biological mass becomes uniquely defined by a single particle stored in the tile representations in datastore 125.

Figure 6B:
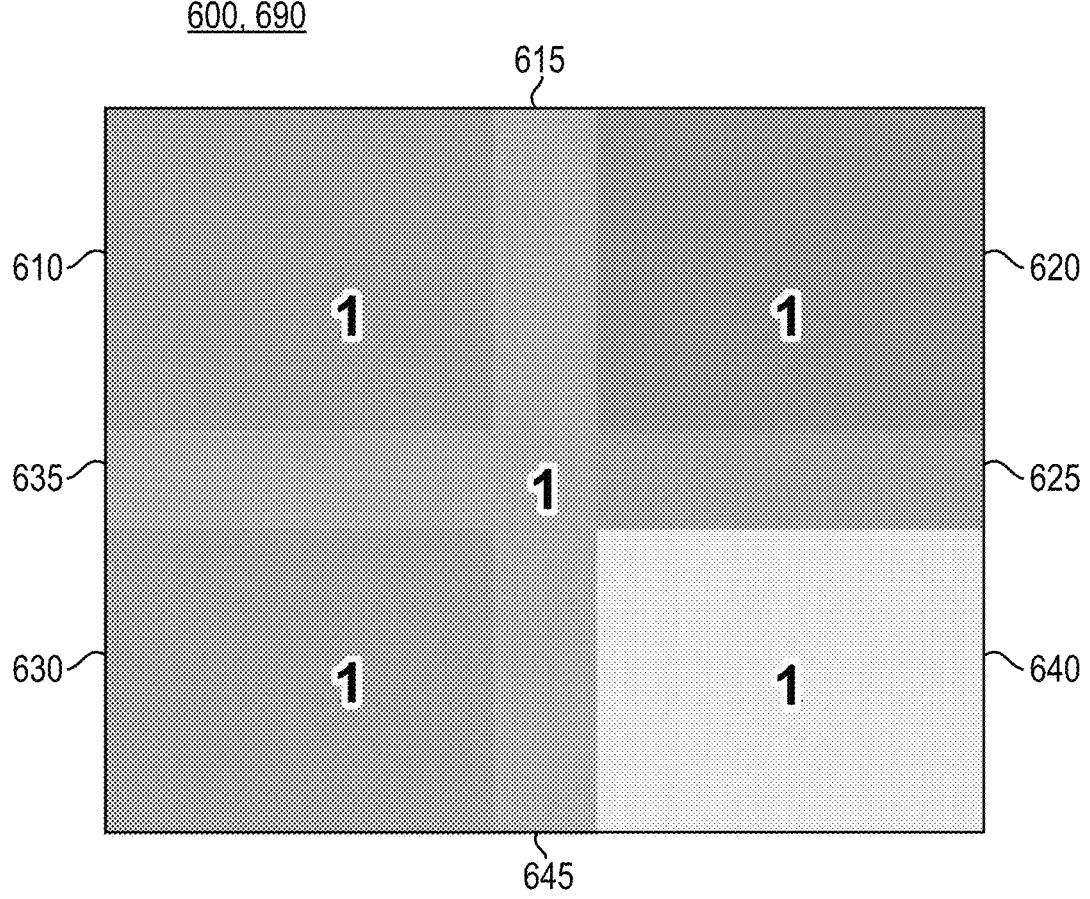

In the example of FIG. 6B, the method 690 keeps or merges the overlapping areas 615 and 635 for the top left tile 610 and removes the associated overlap areas for the top right 620 and lower left 630 neighbor tiles. That is, method 690 applies above-described steps (i)-(iv) to overlap areas 615 and 635 and the interior corner of tile 610, and defines particles in the light shaded areas illustrated along tile's 610 right-hand edge and bottom edge. Method 690 crops the counterpart overlapping area from along the left-hand edge of top right tile 620 and crops the counterpart overlapping area from along the top edge of lower left tile 630. The resulting compressed image data/adaptive sampling representation of tile 610 is stored in datastore 125 by module 121 implementing method 690. Similarly, method 690 applies steps (i)-(iv) to overlap area 625 and defines particles in the light shaded area illustrated along the bottom edge of top right tile 620. Method 690 merges the so defined particles and light shaded area into top right tile 620 and crops the counterpart overlapping area from the upper edge of lower right tile 640. Method 690 (module 121) stores the resulting compressed image data/adaptive sampling representation of top right tile 620 in datastore 125 and stores the cropped adaptive sampling representation of lower right tile 640 in datastore 125. Method 690 applies steps (i)-(iv) to overlap area 645 and defines particles in the light shaded area illustrated along the right-hand edge of lower left tile 630. Method 690 merges the so defined particles and light shaded area into lower left tile 630 and crops the counterpart overlapping area from the left-hand edge of lower right tile 640. Method 690 (module 121) stores the resulting compressed image data/adaptive sampling representation of lower left tile 630 and that of lower right tile 640 in datastore 125.

According to the above improved embodiment, all tiles (adaptive sampling representations thereof) as resultingly stored in datastore 125 by module 121 and method 690 have the same size except the ones along the far right-hand edge of the acquisition and the ones along the bottom edge of the acquisition. The lighter shades of FIG. 6B illustrate where the merging and cropping was done (by module 121 applying method 690). In particular, top left tile 610 (including the shaded areas 615, 635 merged with the tile) remains unchanged in size. Top right tile 620 (including shaded area 625 merged therewith) is cropped to be narrower in size. Lower left tile 630 (including shaded area 645 merged therewith) is cropped in length. Lower right tile 640 is cropped in width and length.

Returning to FIG. 3B, at step 122, the tile processing module determines a relative tile position with respect to other tiles. To accomplish that, for a given tile, step 122 computes a maximum intensity projection of the tile in multiple spatial directions and for each edge where there will be a neighboring tile. Next, tile processing module step 122 computes tile pair-wise registration parameters with already acquired neighboring tiles. Specifically, for each edge of the given tile where there is a respective acquired neighboring tile, the step 122 correlates the computed max intensity projection of the edge of the tile to a computed max intensity projection of a corresponding edge of the respective acquired neighboring tile. By correlating corresponding computed max intensity projections of pertinent edges of a given tile and its neighboring tiles, embodiments provide increased precision of the relative tile position of the tile with respect to its neighboring tiles. Module steps 122, 124 store the computed pair-wise registration parameters in datastore 125. In embodiments, the tile processing module 122 registers the tile with other tiles by: (a) during source image acquisition, obtaining pairwise registration between each neighboring tile using the computed max intensity projections, and (b) subsequently to source image acquisition, globally optimizing for a reliability measure, resulting in the optimal position of each tile computed with a single loading of each tile. Further details are discussed below with respect to image stitching.

Continuing with tile by tile processing during source image acquisition in embodiments, tile processing module step 123 segments objects of interest from the adaptive sampling representation of the tile (output from step 121). The module 123 applies a classifier in a manner segmenting objects from the given tile including extracting object features and object positions. Object features can include for non-limiting example, diameter, shape, volume, etc. of detected objects. In some embodiments, module 123 further computes position of a segmented object using tile positions output from step 122 and stored in the datastore 125. In embodiments, the classifier may be formed by an image filtering operation followed by a thresholding. In other embodiments, the classifier is formed by manually annotating a subset of the tiles after compression of tile areas, and training a machine learning classifier to perform the segmentation directly on the given tile at step 123. Other classifiers are suitable as further discussed below with regard to object segmentation.

In a preferred embodiment, step 123 stores in datastore 125: (i) the output of the classifier (object segmentation generally) which is a binary mask directly computed in APR (so efficient), and (ii) indications of physical aspects and characteristics of the segmented objects, i.e., positions and features, computed from the binary mask. Storing the binary mask with the compressed image data (adaptive sampling representation of the tile) in datastore 125 is very space efficient compared to double the memory space required for storing segmented objects (images) and an uncompressed subject image.

For each tile as processed, tile processing module step 124 stores in datastore 125 in computer memory, (a) the adaptive sampling representation of the tile output from step 121, (b) determined compression parameters for the tile from step 121, (c) an indication of position in 3D space of the tile, i.e., relative tile position of step 122, and (d) segmented objects of interest output from step 123. In one embodiment, the datastore 125 holds a list of segmented objects, extracted object features, and object positions tallied across tiles. As such, the datastore 125 holds individual tile positions and reduced amounts of the image data 110 instead of storing the raw data of source images 103 of the subject biological mass.

As illustrated in FIG. 3A, in some embodiments, the effects of tile processing module 121, 122, 123, 124 configure datastore 125 to serve as part of an image compression apparatus or tool or service 310, 130, 320. In embodiments, specific portions of the image data 110 may additionally be user-selectively read and displayed 305 from the compressed form as stored in datastore 125. See further details below regarding Visualization 305. In embodiments, interface 120 and tile processing module 121, 122, 123, 124 are accomplished during image acquisition by source machine 101 while remaining processing of system/method 1000 is accomplished post-acquisition of the source image 103 as will be made clear below.

Continuing with FIG. 3B, an aggregation module 130 is communicatively coupled to the datastore 125. The aggregation module 130 aggregates the segmented objects in the datastore 125 and forms a working list replacing the initial tally list. For objects that appear twice or more on neighboring tile areas, the aggregation module 130 automatically merges the objects together by means of a matching algorithm. For non-limiting example, embodiments (aggregation module 130) employ matching algorithms of the type nearest neighbor where each object is embedded in a feature space with its position, size and shape. Matches can be reliably validated using the ratio between the nearest neighbor and the second nearest neighbor; if the ratio is above some predefined threshold (usually 0.7), then the match is considered reliable and matched objects are merged.

Other matching algorithms or means for merging the objects at module or step 130 are suitable.

Returning to FIG. 3B, the system/method 1000 employs a merger 140 (also referred to as reconstructor 320, FIG. 3A) responsive to the aggregation module 130. Merger (module or step) 140, 320 merges the tiles of the adaptive sampling representations with a single loading of tiles (i.e., as represented by the datastore 125 data) and therefrom forms an output assembly (file, stream, or the like) or output image (generally) 150 of a complete image at full resolution of the subject biological mass. The merging or reconstruction 320 by merger 140 includes stitching tiles together. The merging is in a manner that supports converting back from the merged tiles to the voxel data of the image volumes of working memory 105. The single loading of tiles approach to form output image 150 relieves necessity of additional computer memory and/or processor resources for any of: storing, retrieving, communicating, distributing, processing, analyzing, displaying, and combinations thereof of the complete image 150. Merger 140/reconstructor 320 may also arrive at the complete image 150 at lower resolutions as desired for some applications. Other embodiments alternatively merge the adaptive sampling representations, i.e., APR files, directly. See further details below with regard to Image merging.

Embodiments may interface at 350, 355 with a registration pipeline, working algorithms, other systems, and the like for non-limiting example. The registration pipeline aligns images of a same category of biological subjects or masses. With such registration, the output data file (complete image) 150 is aligned with like subject images in a common coordinate framework, and the segmented objects (from aggregation module 130) are mapped to counterpart objects in the registration pipeline. The alignment and mapping advantageously enable counting of cells in a subject body part, and the like. Other uses and advantages of embodiments are in the purview of one skilled in the art given the current disclosure.

Presented next are further implementation details in addition to or as a variation of the modules, steps, and elements of FIGS. 3A and 3B in different embodiments of the present invention.

Automatic Image Conversion

The adaptive sampling of the APR is computed based on gradients in the raw image signal, relative to the local intensity scale used to normalize errors. Both the gradients and local intensity scale must be estimated numerically from the acquired image. This is highly sensitive to noise, which leads to high-frequency fluctuations in regions where the underlying (true) signal is perfectly flat. The current implementation uses a smoothing B-spline approximation of the signal to reduce the impact of noise on the gradient and local intensity scale.

The conversion from voxel image to APR depends on a number of parameters. Most of these can reliably remain fixed for a given optical system or experiment (e.g., voxel size, background intensity level, and the degree of smoothing in the B-spline computation). However, smoothing is not sufficient to fully circumvent the effects of noise in the signal. Therefore, in order to avoid oversampling due to normalization of small gradients, the gradients and local intensity scale are thresholded from below. This introduces two additional threshold parameters, one for each quantity. In contrast to the other parameters, optimal values of these thresholds are highly dependent on the local signal content.

Hence, for large-scale experiments where manual tuning is infeasible, automatic estimation of these parameters is necessary.

The optimal threshold values are those that best separate the distribution of values (gradient and local intensity scale) stemming from the actual signal and fluctuations due to noise. Lower threshold values lead to adaptation to noise and suboptimal compression, while higher values lead to undersampling and loss of information. In principle, any automatic thresholding algorithm (local or global) may be used to estimate the optimal values. However, as the distributions are highly dependent on both the optical setup and local characteristics of the sample, algorithms relying on strict assumptions about the form of the distribution are inappropriate. Embodiments employ the minimum cross entropy thresholding algorithm by Li et al [10], due to its proven robustness, simplicity, and computational efficiency.

Image Stitching 122, 310

Samples are scanned and acquired using a raster scan pattern, or any pattern that allows to cover the entirety of the desired area, where each tile is sequentially acquired. Applicant's pipeline supports sparse tiling as long as each tile is connected to the others by at least one of its sides and was adapted for APR by drawing inspiration from [1]. The neighboring map is first computed for each tile (i.e., the side neighbors of each tile). Then, for each pair of neighboring tiles the displacements to align these tiles (x, y, z) are computed by using the phase cross-correlation [2] on the maximum intensity projections ($I_x$, $I_y$, $I_z$). Other alignment methods are also used for improved performance depending on the biological or medical images characteristics. Such alignment methods include, but are not limited to, feature (e.g., SIFT) matching (e.g., RANSAC), machine learning approaches.

If artifacts are present in the volume (e.g., air bubbles embedded around the sample) then a masked version of the phase cross-correlation is used [3].

Maximum intensity projections are pre-computed (only on the expected overlapping area to remove noise in the phase cross-correlation) to allow the stitching to be performed with a single loading of each tile. Doing that, for each pair of neighboring tile, a total of 6 displacements (2 for x, 2 for y and 2 for z) are computed. The most reliable one is kept, where the reliability is computed as the least square difference between registered max projections. The reliability can also be computed with other metrics such as, but not limited to, the ratio between the maximum of the difference between the registered and original maximum intensity projection and twice the maximum of the original image which Applicant found to be very effective for sparse samples.

The displacements are stored in three graphs (one for each spatial dimension) where each vertex corresponds to a given tile and each edge corresponds to the displacement between the two tiles. A corresponding reliability graph is constructed for each spatial dimension. Finally, each displacement graph is globally optimized by stitcher 310 using the maximum spanning tree on the reliability graphs in order to satisfy the inner problem constraint where each loop in the graph should sum to 0.

For the stitching, each step is done fully using the APR except to compute the phase cross-correlation. For this step, the maximum intensity projection is computed on APR and then a 2D pixel image is reconstructed. Regenerating pixel data is not penalizing in this case because it is only in 2D, so it has a low memory footprint.

Finally, as mentioned previously in FIGS. 3A and 3B, tile positions are stored in a datastore 125 and can be used later to compute segmented object position or for visualization at 305.

Object Segmentation

For segmenting objects such as labelled cells, a particle classification strategy is used in one embodiment. A random forest with 100 estimators [4] is trained on a small portion of the data that was previously manually annotated sparsely.

The proposed pipeline does not merge tiles before performing the segmentation because the segmentation is done directly after a tile has been completely acquired, while the next tile is being acquired. Objects' features and positions are extracted and a merging strategy inspired by [5] was developed to merge the high-level information without actually merging the APR data. For each neighboring tile, the two nearest neighbors (NN) of each object in the overlapping area of the first tile are computed in the set of objects that are in the overlapping area of the second tile. If the ratio between the second NN and the first NN is greater than a threshold (typically 0.7) and if the object centers are closer than a threshold distance (typically a quarter of the object size), then objects are considered to be the same and automatically merged. Objects that are touching an edge on an overlapping area are automatically discarded to avoid counting them twice. This strategy was validated on a synthetic data-set as demonstrated in FIG. 2.

Figure 2:
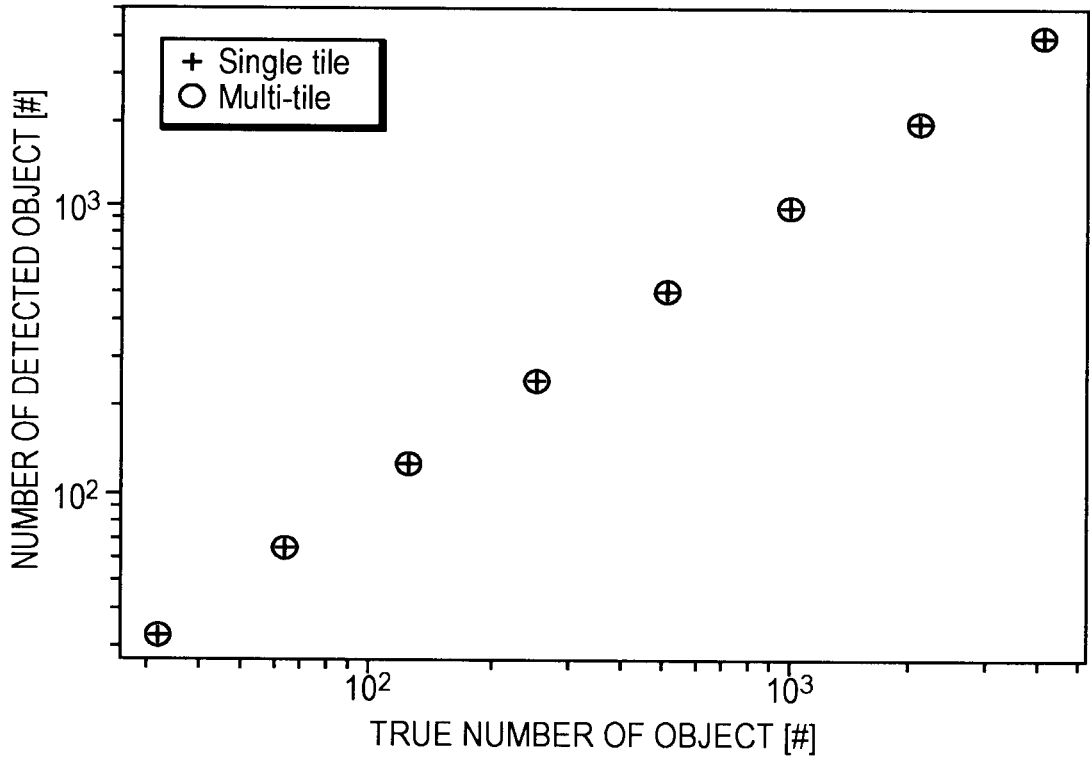
FIG. 2 is a graph illustrating the merging of segmented objects on multi-tile data of subject medical images. The number of software detected objects in the medical images is plotted against the true number of objects. The number of detected objects on the original image data before it was sliced to create a multi-tile data-set is also reported. Computational ratio is the ratio of the total number of voxel before compression and the total number of particles after compression.

FIG. 2 is a graph illustrating the merging of segmented objects on multi-tile data of subject medical or biomedical images. A synthetic multi-tile data-set was randomly created with various numbers of objects and random shifts. Each tile is individually segmented and objects are then merged on the overlapping area (after computing the correct registration as described above). The number of detected objects is plotted against the true number of objects. The number of detected objects on the original data (before it was sliced to create a multi-tile data-set) is also shown in the graph of FIG. 2 as a reference.

Image Merging

Some applications such as registering the sample to an atlas 350 or the like 355 require a merged volume. Fortunately, these applications 350, 355 usually require a lower sample resolution, avoiding the need to regenerate the original image data footprint. Each tile is efficiently voxel reconstructed at a lower resolution by simply selecting the right APR level and interpolated later on if a precise voxel size is required. Tiles are then merged using any merging strategy such as taking the average or the maximum of the overlapping areas. Preprocessing (e.g. histogram equalization) can be performed prior to the conversion and merging to benefit from APR computation speed up.

Registration to the Atlas 350

The merged mouse brain can be registered to the Allen brain mouse atlas [6] using the AMAP pipeline [7] through the Brainreg front end [8].

Visualization 305

In one embodiment, Napari [9] is used as a front-end for visualization 305. It requires an object with a slicing property to allow for lazy loading, thus avoiding the need to regenerate the complete sample in voxel space. So called 'lazy loading' is the reading of the compressed image data (output from step 121 and stored in datastore 125) for displaying the same.

Stitching Benchmarks

Stitching speed was compared with TeraStitcher [1] with steps 1-5 (corresponding to finding the stitching parameters without merging the data). Multiple instances of TeraStitcher can be run at the same time using openmpi, the best performances were obtained using 4 cores. Applicants created a synthetic data set consisting in 4×4 tiles of 2048× 512×512 unit 16 voxels (around 1Gb/tile) with various computational ratios (by varying the number of objects). Computational ratio is the ratio of the total number of voxels before compression and the total number of particles after compression. Voxel data was converted to APR using automatic parameter determination described above (see Automatic image conversion section).

Figure 1:
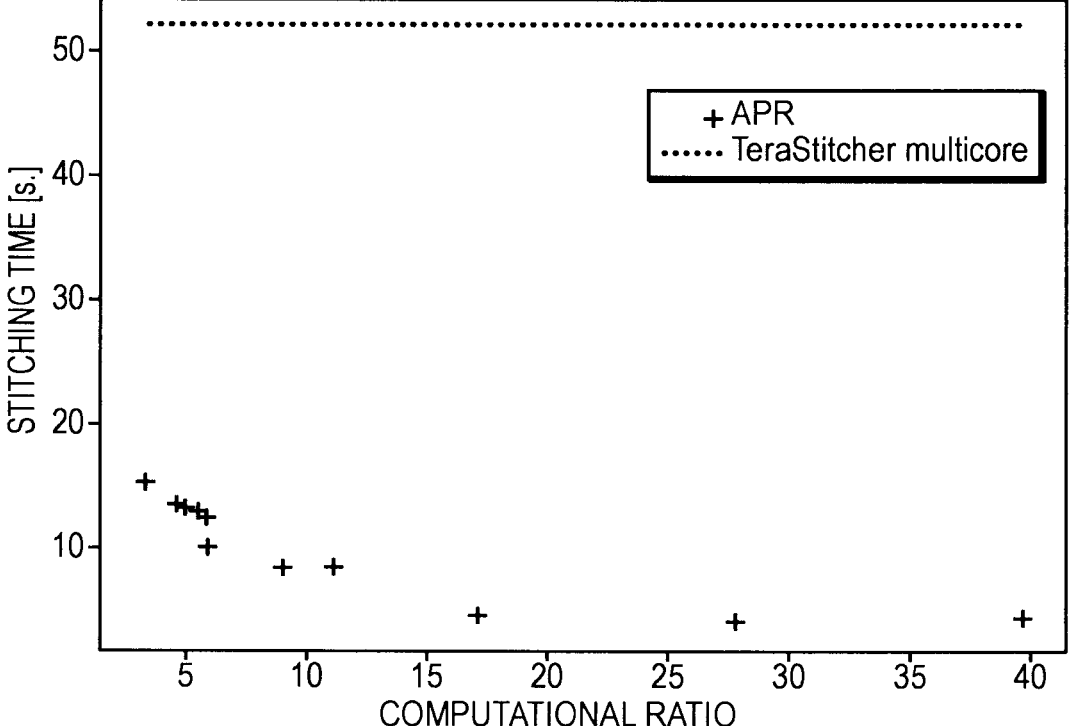
FIG. 1 is a graph of APR (Adaptive Particle Representation) stitching time evaluated for different computational ratio (CR) and compared to that of TeraStitcher. Computational ratio is the ratio of the total number of voxels before compression and the total number of particles after compression.

With reference to FIG. 1, APR stitching time is evaluated for different computational ratios (CR) and compared to the stitching time of TeraStitcher. The graph of FIG. 1 shows a speed-up from 20 to 1000 compared to TeraStitcher in stitching time of embodiments.

In FIG. 6 of the priority applications herein incorporated by reference in their entirety, the drawing further illustrates APR conversion, Stitching, Segmentation, and Atlas registration in an embodiment. Shown there is an end-to-end pipeline for analyzing large 3D cleared tissue samples of whole mouse brains or large human brain sections. The disclosed system and method achieve 100+ times faster computation.

The Stitching step or module in the above end-to-end pipeline stitches directly on the APR produced representation of the subject image. The Stitching module supports any tiling pattern. Advantageously, the Stitching module is highly efficient reading each tile only once.

The Segmentation module of the above end-to-end pipeline operates directly on the APR produced representation of the subject image and segments (extracts) objects, object features, and object positions from the subject image. Manual annotations by users can be created efficiently directly on the APR produced representation.

Lastly, Atlas registration 350 is shown in the example end-to-end pipeline. Lower resolution pixel data can be reconstructed and merged directly from a multi-tile APR representation of the subject image. This enables Atlas registration pipelines such as AMAP through Brainreg (as a front end) to be used and mapped back to the APR data.

As a result, the methods and systems embodying the present invention provide an efficient image analysis pipeline based on APR for processing large 3D datasets with a speed-up (improved processing rate) of 20 to 1000 times relative to existing solutions and a lowering of storage (memory) requirements. Such embodiments are particularly well suited for large-scale imaging projects.

The Appendix of the priority applications (herein incorporated by reference in their entireties) provides further details of embodiments of the present invention.

Computer Support

Figure 4:
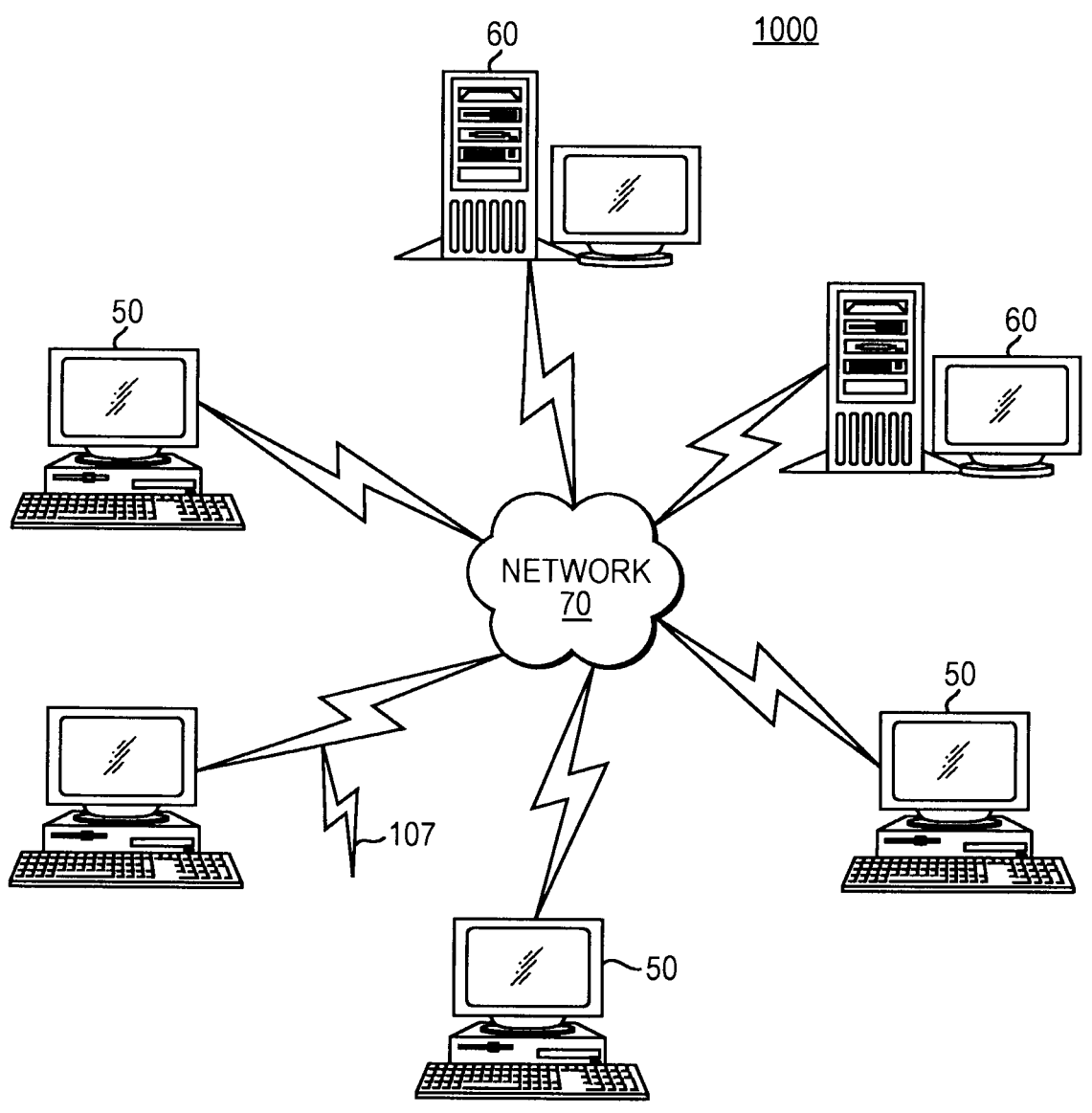
FIG. 4 is a schematic view of a computer network environment in which embodiments are deployed.

FIG. 4 illustrates a computer network or similar digital processing environment in which embodiments of the present invention may be implemented.

Client computer(s)/devices 50 and server computer(s) 60 provide processing, storage, and input/output devices executing application programs, core programs, and the like. Client computer(s)/devices 50 may include imaging sources such as above discussed medical imaging machines 101. Client computer(s)/devices 50 can also be linked through communications network 70 to other computing devices, including other client devices/processes 50 and server computer(s) 60. Communications network 70 can be part of a remote access network, a global network (e.g., the Internet), cloud computing servers or service, a worldwide collection of computers, Local area or Wide area networks, and gateways that currently use respective protocols (TCP/IP, Bluetooth, etc.) to communicate with one another. Other electronic device/computer network architectures are suitable.

Figure 5:
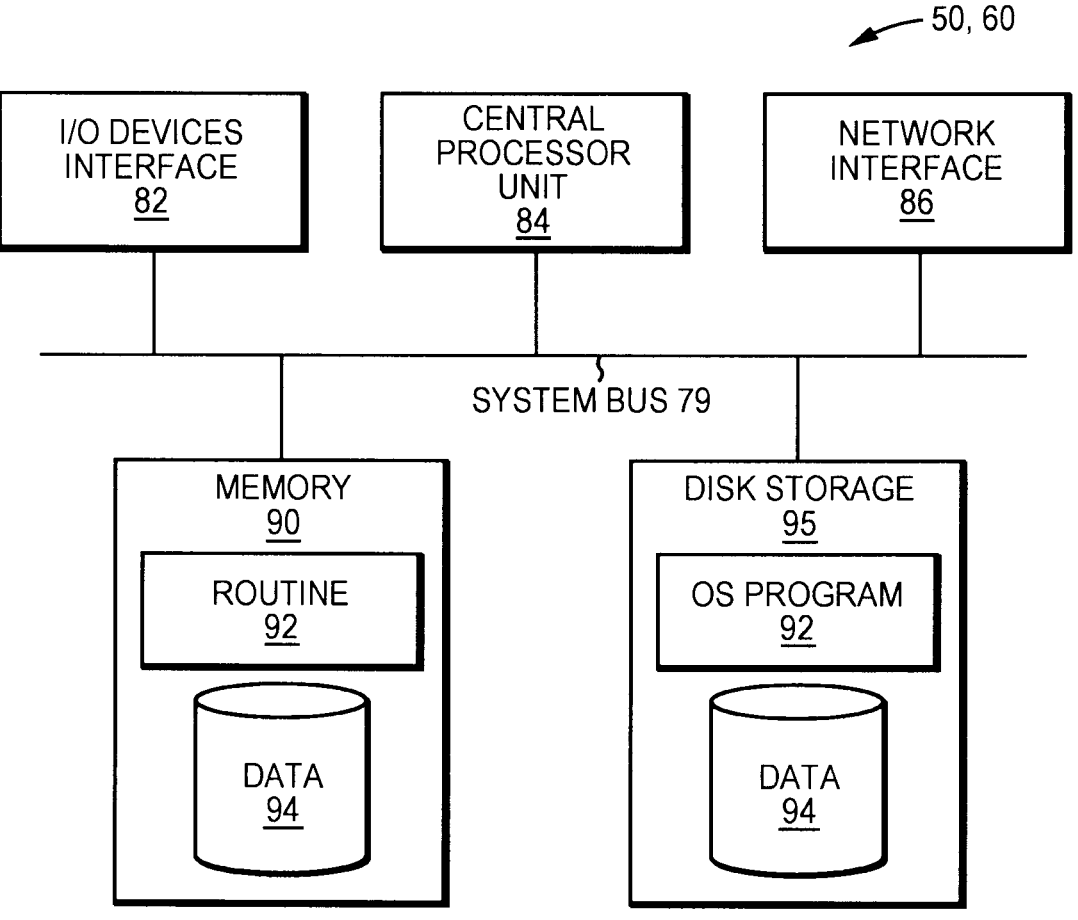
FIG. 5 is a block diagram of a computer node in the computer network of FIG. 4.

FIG. 5 is a diagram of the internal structure of a computer (e.g., client processor/device 50 or server computers 60) in the computer system of FIG. 4. Each computer 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, Network interface 86 allows the computer to connect to various other devices attached to a network (e.g., network 70 of FIG. 4). Memory 90 provides volatile storage for computer software instructions 92 and data 94 used to implement an embodiment of the present invention (e.g., the image processing method, system, techniques, datastore/database, and program code detailed above in FIGS. 3A, 3B, 6A, and 6B). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

In other embodiments, the program product 92 may be implemented as a so-called Software as a Service (SaaS), or other installation or communication supporting end-users.

Given the foregoing description and details, embodiments of the present invention provide many advantages over prior art methods and approaches. For example, embodiments segment objects of interest from image data during source image acquisition as opposed to post-acquisition. Such a novel approach enables scalability and generates readily available results (image objects) at the end of image acquisition.

Embodiments advantageously stitch together and reconstruct the subject image with a single loading of each tile (i.e., the stored compressed image data, stored relative tile positions, compression parameters, stored segmented objects, and stored object positions). In contrast, prior art methods load the tile data two times, namely once for evaluating registration parameters and later at an ending stage in order to merge all tiles to create an image file. Prior art approaches may apply object segmentation and other analysis to the image file. However, merging all the tiles is not necessarily a scalable approach because at some point the image file may become too large to handle or to be saved. Applicants address these shortcomings of the art and keep individual tiles separated. Instead, Applicants' approach merges the segmented object information when needed (e.g., the segmented object that appeared twice or more on overlapping or neighboring tile areas discussed above in module 130 of FIG. 3A). Applicants' approach scales well because each tile is processed independently (or with its neighbors) as long as the tile processing keeps up with the data throughput of the source machine 101 which is achievable when using adaptive sampling representation of tiles (e.g., APR).

The teachings of all patents, published applications and references cited herein are incorporated by reference in their entirety.

REFERENCES

[1] Bria, A. & Iannello, G. TeraStitcher—a tool for fast automatic 3d-stitching of teravoxel-sized microscopy images. BMC Bioinformatics 13 (2012). https://doi.org/10.1186/1471-2105-13-316.

[2] Guizar-Sicairos, M., Thurman, S. T. & Fienup, J. R. Efficient subpixel image registration algorithms. Optics Letters 33, 156 (2008). https://doi.org/10.1364/01.33.000156.

[3] Padfield, D. Masked object registration in the fourier domain. IEEE Transactions on Image Processing 21, 270612718 (2012). https://doi.org/10.1109/tip.2011.2181402.

[4] Fernandez-Delgado, M., Cernadas, E., Barro, S. & Amorim, D. Do we need hundreds of classifiers to solve real world classification problems? Journal of Machine Learning Research 15, 313313181 (2014). http://jmlr.org/papers/v15/delgadol4a.html.

[5] Lowe, D. G. Distinctive image features from scale-invariant keypoints. International Journal of Computer Vision 60, 911110 (2004). https://doi.org/10.1023/b:visi.0000029664.99615.94.

[6] Lein, E. S. et al. Genome-wide atlas of gene expression in the adult mouse brain. Nature 445, 1681176 (2006). https://doi.org/10.1038/nature05453.

[7] Niedworok, C. J. et al. aMAP is a validated pipeline for registration and segmentation of high-resolution mouse brain data. Nature Communications 7 (2016). https://doi.org/10.1038/ncomms11879.

[8] Tyson, A. L. et al. Tools for accurate post hoc determination of marker location within whole-brain microscopy images (2021). https://doi.org/10.1101/2021.05.21.445133.

[9] Sofroniew, N. et al. napari/napari: 0.4.9rc0 (2021). URL https://zenodo.org/record/3555620.

[10] Li, C. H. and Tam, P. K. S., 1998. An iterative algoritym for minimum cross entropy thresholding. Patternrecognition letters, 19(8), pp. 771-776.

While example embodiments have been particularly shown and described, it will be understood by those skilled in the art that various changes in form and details may be made therein without departing from the scope of the embodiments encompassed by the appended claims.

What is claimed is:

1. A computer-implemented image handling method, comprising:

for given image data of a biological mass, obtaining a sequence of two-dimensional image units at increasing depth along an axis in a third spatial dimension, each two-dimensional image unit being an n×m pixels frame in a respective parallel plane orthogonal to the axis, obtaining different sequences of two-dimensional image units at increasing depth along respective orthogonal axes, each two-dimensional image unit of a sequence being an n×m pixels frame in a respective parallel plane orthogonal to the respective axis of the sequence, different sequences having different orthogonal axes at different tile positions across the respective planes, the obtaining resulting in a plurality of sequences serving as tiles and representative of image volumes capturing in three spatial dimensions different portions of the biological mass, different sequences of the plurality being different tiles representing different image volumes;

during source image acquisition, automatically by a computer processor processing each tile independently by:

i) compressing image data of tile areas of low information content and maintaining high resolution of high information content areas resulting in an adaptive sampling representation of the tile, ii) determining relative tile position with respect to other tiles, iii) segmenting the adaptive sampling representation of the tile for objects of interest, the segmenting including extracting object features and respective object positions, iv) storing in a datastore in computer memory, the adaptive sampling representation of the tile, the determined tile position, the segmented objects, the extracted object features, and object positions, the storing being in a manner such that the datastore stores individual tile positions and reduced amounts of the given image data instead of storing source images of the biological mass;

aggregating the segmented objects stored in the datastore, wherein aggregating includes automatically merging segmented objects that appear twice or more on neighboring tiles resulting in a working list of segmented objects stored in the datastore; and based on the adaptive sampling representations of tiles, tile positions, and working list of segmented objects as stored in the datastore, single loading tiles and forming therefrom a complete image at full resolution of the biological mass, in part or in whole, the single loading of tiles relieving necessity of additional computer memory and/or processor resources for any of: storing, retrieving, communicating, distributing, processing, analyzing, displaying, and combinations thereof of the complete image.

2. A method as claimed in claim 1 wherein processing each tile independently further includes:

automatically determining compression parameters used to compress image data of the tile;

storing the determined compression parameters in the datastore; and automatically comparing the resulting adaptive sampling representation and source image data in a manner validating that the adaptive sampling representation captures required information of the given image data.

3. A method as claimed in claim 1 wherein determining relative tile position of a tile includes:

computing a maximum intensity projection of the adaptive sampling representation of the tile in multiple spatial directions and for each edge of the tile where there is a neighboring tile;

computing tile pair-wise registration parameters with already acquired and adaptively sampled neighboring tiles by: for each edge of the tile where there is a respective acquired neighboring tile, correlating the computed maximum intensity projection of the edge of the tile to a computed max intensity projection of a corresponding edge of the respective acquired neighboring tile, resulting in increased precision of the relative tile position of the tile with respect to neighboring tiles; and storing the computed tile pair-wise registration parameters in the datastore.

4. A method as claimed in claim 3 further comprising:

subsequent to image acquisition, globally optimizing all the stored pair-wise registration results for a reliability measure, such that all tile positions are precisely corrected, enabling: (a) stitching of image data corresponding to tiles, (b) proper reconstruction of the whole biological mass; and (c) reliable extraction of high level information on the imaged biological mass, such as, but not limited to, volume of the biological mass, and number of segmented objects inside; and wherein step C is performed after global optimization.

5. A method as claimed in claim 4 wherein stitching is performed with the single loading of each tile.

6. A method as claimed in claim 1 wherein the given image data comprises biological or medical images acquired and generated by any of: optical microscopy, electron microscopy, x-ray, computed tomography, positron emission tomography, optical coherence tomography, magnetic resonance imaging, ultrasound, and other digital imaging techniques; and wherein for a subject tile, step A and step B are accomplished during acquisition of the biological or medical images, and step C is performed subsequent to acquisition of images corresponding to the subject tile.

7. A method as claimed in claim 1 wherein the given image data further includes any one or combination of: color, annotations, text, graphics, temporal feature, and the like.

8. A method as claimed in claim 1 wherein the biological mass is any of: a tissue sample, whole mouse brain, human brain section, other mammalian brain portion, and other biological material of interest.

9. A method as claimed in claim 1 further comprising: in addition to compressing tile areas, independently compressing different fluorescent channels of the given image data.

10. A method as claimed in claim 1 further comprising: in addition to compressing tile areas, compressing across on different time periods of the given image data.

11. A method as claimed in claim 1 wherein compressing tile areas of low information content includes employing the Adaptive Particle Representation (APR) technology.

12. A method as claimed in claim 1 wherein the segmenting applies a classifier on the adaptive sampling representations of tiles, and the classifier is formed by one of:

(i) an image filtering operation followed by a thresholding, and (ii) a machine learning algorithm, such as, but not limited to, random forest, support vector machine, and neural networks, that was trained on similar data.

13. A method as claimed in claim 1 wherein the aggregating of segmented objects automatically merges objects by a matching algorithm.

14. A method as claimed in claim 1 further comprising computing position of a segmented object using tile positions stored in the datastore.

15. A method as claimed in claim 1 further comprising displaying any one or combination of: (a) an image of the biological mass based on the stored adaptive sampling representations of the tiles, and tile positions stored in the data store, and (b) an image of the segmented objects based on data of the segmented objects stored in the datastore.

16. A method as claimed in claim 1 further comprising interfacing with a registration pipeline that aligns volume of biological masses in a common coordinate framework and mapping the segmented objects in the common coordinate framework.

17. A method as claimed in claim 1 wherein the complete image is alternatively or optionally displayed at lower resolution.

18. A method as claimed in claim 1 further comprising: reading and displaying a specific portion of the given image data from the adaptive sampling representation.

19. A method as claimed in claim 1 wherein the stored adaptive sampling representation of each tile is merged and cropped on overlapping tile areas so that a physical position in the biological mass is uniquely described by a single particle in the adaptive sampling representations of tiles stored in the datastore.

20. A computer-based biomedical image handling system, comprising:

an interface receiving or accessing subject image data of a biological mass, the interface obtaining a sequence of two-dimensional image units at increasing depth along an axis in a third spatial dimension, each two-dimensional image unit being an n x m pixels frame in a respective parallel plane orthogonal to the axis, the obtaining including obtaining different sequences of two-dimensional image units at increasing depth along respective orthogonal axes, each two-dimensional image unit of a sequence being an n x m pixels frame in a respective parallel plane orthogonal to the respective axis of the sequence, different sequences having different orthogonal axes at different tile positions across the respective planes, the obtaining resulting in a plurality of sequences serving as tiles and representative of image volumes capturing in three spatial dimensions different portions of the biological mass, different sequences of the plurality being different tiles representing different image volumes;

a tile processing module communicatively coupled to the interface, and during image acquisition, the tile processing module being automatically executed by a digital processor and processes each tile independently by:

i) compressing image data of tile areas of low information content and maintaining full resolution of high information content areas resulting in an adaptive sampling representation of the tile;

ii) determining relative tile position with respect to other tiles;

iii) segmenting the adaptive sampling representation of the tile for objects of interest, the segmenting including extracting object features and respective object positions; and iv) storing in a datastore in computer memory the adaptive sampling representation of the tile, the determined tile position, the segmented objects, the extracted object features, and object positions, the storing being in a manner such that the datastore stores individual tile positions and reduced amounts of the subject image data instead of storing source images of the biological mass;

an aggregation module responsive to the tile processing module, the aggregation module aggregating the segmented objects stored in the datastore, wherein aggregating includes automatically merging segmented objects that appear twice or more on neighboring tiles resulting in a working list of segmented objects, object positions, and features stored in the datastore; and an output assembly having contents based on the adaptive sampling representations of tiles, tile positions, and the working list of segmented objects as stored in the datastore, and the output assembly being configured such that a single loading of tiles therefrom forming a complete image at full resolution of the biological mass in part or whole, the single loading of tiles relieving necessity of additional computer memory and/or processor resources for any of: storing, retrieving, communicating, distributing, processing, analyzing, displaying, and combinations thereof of the complete image.

21. A computer-based biomedical image handling system of claim 20 wherein the interface receives or accesses the subject image data from a source machine, computer memory, archive, or any combination thereof.

22. A computer-based biomedical image handling system of claim 20 wherein:

the subject image data comprise biological or medical images acquired and generated by a source machine using any of: x-ray, computed tomography, positron emission tomography, optical microscopy, electron microscopy, optical coherence tomography, magnetic resonance imaging, ultrasound, and other digital imaging techniques; and the tile processing module is configured to process in near real-time of acquisition of the biological or medical images.

23. A computer-based biomedical image handling system of claim 20 wherein the subject image data further includes any one or combination of: color, annotations, text, graphics, temporal feature, and the like.

24. A computer-based biomedical image handling system of claim 20 wherein the biological mass is any of: a tissue sample, whole mouse brain, human brain section, other mammalian brain portion, and other biological material of interest.

25. A computer-based biomedical image handling system of claim 20 wherein the tile processing module independently applies the adaptive sampling compression on different fluorescent channels of the subject image data.

26. A computer-based biomedical image handling system of claim 20 wherein the tile processing module applies the adaptive sampling compression across different time periods of the subject image data.

27. A computer-based biomedical image handling system of claim 20 wherein the tile processing module employs Adaptive Particle Representation (APR) technology to compress image data of tile areas of low information content.

28. A computer-based biomedical image handling system of claim 20 wherein the system further allows reading and displaying of a specific portion of the subject image data from the adaptive sampling representations stored in the datastore.

29. A computer-based biomedical image handling system of claim 20 wherein the complete image from the output assembly is optionally or alternatively displayed at a lower resolution.

30. A computer-based biomedical image handling system of claim 20 further comprising a registration interface enabling: (i) interfacing with a registration pipeline that aligns volume of various biological masses in a common coordinate system, and (ii) mapping the segmented objects in the common coordinate system.

31. A computer-based biomedical image handling system of claim 20 wherein the tile processing module segments objects by applying a classifier on the adaptive sampling representations, the classifier being formed by one of:

(i) an image filtering operation followed by a thresholding, and (ii) a machine learning algorithm, such as, but not limited to, random forest, support vector machine, and neural networks that were trained on similar data.

32. A computer-based biomedical image handling system of claim 20 wherein the aggregation module aggregating the segmented objects automatically merges objects by a matching algorithm.

33. A computer-based biomedical image handling system of claim 20 wherein the tile processing module further computes position of a segmented object using tile positions stored in the data store.

34. A computer-based biomedical image handling system of claim 20 further comprising a display module coupled to display an image of the biological mass based on the stored adaptive sampling representations of tiles, tile positions stored in the data store, and data of the segmented objects stored in the data store.

35. A computer-based biomedical image handling system as claimed in claim 20 wherein the tile processing module stores in the datastore the adaptive sampling representation of each tile merged and cropped on overlapping tile areas so that a physical position in the biological mass is uniquely described by a single particle in the adaptive sampling representations of tiles in the datastore.

36. A computer-implemented image handling method, comprising:

for given image data of a biological mass, obtaining a sequence of two-dimensional image units at increasing depth along an axis in a third spatial dimension, each two-dimensional image unit being an n x m pixels frame in a respective parallel plane orthogonal to the axis, obtaining different sequences of two-dimensional image units at increasing depth along respective orthogonal axes, each two-dimensional image unit of a sequence being an n x m pixels frame in a respective parallel plane orthogonal to the respective axis of the sequence, different sequences having different orthogonal axes at different tile positions across the respective planes, the obtaining resulting in a plurality of sequences serving as tiles and representative of image volumes capturing in three spatial dimensions different portions of the biological mass, different sequences of the plurality being different tiles representing different image volumes;

automatically by a computer processor processing each tile independently by:

i) compressing image data of tile areas of low information content and maintaining high resolution of high information content areas resulting in an adaptive sampling representation of the tile, ii) determining relative tile position with respect to other tiles, iii) segmenting the adaptive sampling representation of the tile for objects of interest, the segmenting including extracting object features and respective object positions, iv) storing in a datastore in computer memory, the adaptive sampling representation of the tile, the determined tile position, the segmented objects, the extracted object features, and object positions, the storing being in a manner such that the datastore stores individual tile positions and reduced amounts of the given image data instead of storing source images of the biological mass;

aggregating the segmented objects stored in the datastore, wherein aggregating includes automatically merging segmented objects that appear twice or more on neighboring tiles resulting in a working list of segmented objects stored in the datastore; and based on the adaptive sampling representations of tiles, tile positions, and working list of segmented objects as stored in the datastore, single loading tiles and forming therefrom a complete image at full resolution of the biological mass, in part or in whole, the single loading of tiles relieving necessity of additional computer memory and/or processor resources for any of: storing, retrieving, communicating, distributing, processing, analyzing, displaying, and combinations thereof of the complete image.

37. A method as claimed in claim 36 wherein for a subject tile step A and step B are performed during source image acquisition, and step C is performed subsequent to image acquisition of images corresponding to the subject tile.

38. A computer-based biomedical image handling system, comprising:

an interface receiving or accessing subject image data of a biological mass, the interface obtaining a sequence of two-dimensional image units at increasing depth along an axis in a third spatial dimension, each two-dimensional image unit being an n x m pixels frame in a respective parallel plane orthogonal to the axis, the obtaining including obtaining different sequences of two-dimensional image units at increasing depth along respective orthogonal axes, each two-dimensional image unit of a sequence being an n x m pixels frame in a respective parallel plane orthogonal to the respective axis of the sequence, different sequences having different orthogonal axes at different tile positions across the respective planes, the obtaining resulting in a plurality of sequences serving as tiles and representative of image volumes capturing in three spatial dimensions different portions of the biological mass, different sequences of the plurality being different tiles representing different image volumes;

a tile processing module communicatively coupled to the interface, the tile processing module being automatically executed by a digital processor and processes each tile independently by:

i) compressing image data of tile areas of low information content and maintaining full resolution of high information content areas resulting in an adaptive sampling representation of the tile;

ii) determining relative tile position with respect to other tiles;

iii) segmenting the adaptive sampling representation of the tile for objects of interest, the segmenting including extracting object features and respective object positions; and iv) storing in a datastore in computer memory the adaptive sampling representation of the tile, the determined tile position, the segmented objects, the extracted object features, and object positions, the storing being in a manner such that the datastore stores individual tile positions and reduced amounts of the subject image data instead of storing source images of the biological mass;

an aggregation module responsive to the tile processing module, the aggregation module aggregating the segmented objects stored in the datastore, wherein aggregating includes automatically merging segmented objects that appear twice or more on neighboring tiles resulting in a working list of segmented objects, object positions, and features stored in the datastore; and an output assembly having contents based on the adaptive sampling representations of tiles, tile positions, and the working list of segmented objects as stored in the datastore, and the output assembly being configured such that a single loading of tiles therefrom forming a complete image at full resolution of the biological mass in part or whole, the single loading of tiles relieving necessity of additional computer memory and/or processor resources for any of: storing, retrieving, communicating, distributing, processing, analyzing, displaying, and combinations thereof of the complete image.

39. A computer-based biomedical image handling system as claimed in claim 38 wherein the subject image data comprise biological or medical images acquired and generated by a source machine; and the tile processing module is configured to process in near real-time of acquisition of the biological or medical images.

\* \* \* \* \*